United States Patent [19]

Lim et al.

[11] 4,139,534

[45] Feb. 13, 1979

[54] PROCESS FOR THE PREPARATION OF 14-HYDROXYMORPHINAN DERIVATIVES

[75] Inventors: Gary Lim; Ivo Monkovic, both of Candiac, Canada

[73] Assignee: Bristol-Myers Company, New York, N.Y.

[21] Appl. No.: 769,808

[22] Filed: Feb. 17, 1977

[51] Int. Cl.$^2$ .................. C07D 221/28; C07D 217/24
[52] U.S. Cl. ........................................ 546/74; 546/91; 546/142; 546/146
[58] Field of Search ........................................ 260/285

[56] References Cited

U.S. PATENT DOCUMENTS

| | | |
|---|---|---|
| 3,634,429 | 1/1972 | Leimgruber et al. ................ 260/285 |
| 3,775,414 | 11/1973 | Monkovic et al. ................ 260/285 |
| 3,819,635 | 6/1974 | Pachter et al. ................ 260/285 |
| 3,919,237 | 11/1975 | Halder ................ 260/285 |
| 3,980,641 | 9/1976 | Monkovic et al. ................ 260/285 |
| 4,058,531 | 11/1977 | Monkovic et al. ................ 260/285 |

OTHER PUBLICATIONS

Fieser et al., Reagents for Organic Synthesis, John Wiley & Sons, N.Y., p. 202, 1967.

Onda et al., Chem. Pharm. Bull. 21, 2359–2365 (1973).
Schnider et al., Helv. Chim Acta 34 2218–2222 (1951).
Schnider et al., Helv. Chim Acta 376 710–720 (1954).
Schnider et al., Helv. Chim Acta 33, 1437–1448 (1950).

*Primary Examiner*—Donald G. Daus
*Assistant Examiner*—Diana G. Rivers
*Attorney, Agent, or Firm*—Robert H. Uloth

[57] ABSTRACT

N-substituted-14-hydroxy-3-substituted-morphinan derivatives have been found to possess potent narcotic agonist or antagonist activity. In particular, the compound N-Cyclobutylmethyl-3,14-dihydroxymorpinan has been found to posess potent agonist/antagonist activity as a non-narcotic analgesic. An improved total snythesis of these compounds is described herein from the starting material 2-(p-methoxybenzyl)-1,2,3,4,5,6,7,8-octahydroisoquinoline. A preferred feature of the process involves borane reduction of 2-cyclobutylcarbonyl-9,10-dihydroxy-1-(p-methoxybenzyl)perhydroisoquinoline (Va) to provide the corresponding cyclobutylmethyl derivative complexed with borane which is converted directly to N-cyclobutyl-methyl-14β-hydroxy-3-methoxymorphinan (LVa) by treating with acid.

19 Claims, No Drawings

PROCESS FOR THE PREPARATION OF 14-HYDROXYMORPHINAN DERIVATIVES

DESCRIPTION OF THE PRIOR ART

1. U.S. Pat. No. 3,775,414 describes a process for the preparation of the identical compounds prepared by the process claimed herein.
2. U.S. Pat. No. 3,819,635 and 3,980,641 describe additional processes for the preparation of the identical compounds prepared by the process claimed herein.
3. Onda et al. Chem. Pharm. Bull. 21, 2359–2365 (1973) report the epoxidation of 1-(p-methoxybenzyl)-2-methyl-1,2,3,4,5,6,7,8-octahydroisoquinoline to produce the two epimeric epoxides

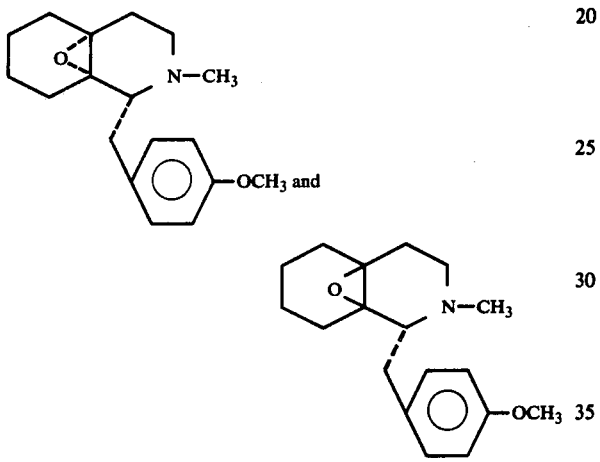

and the diols resulting therefrom having the formulas

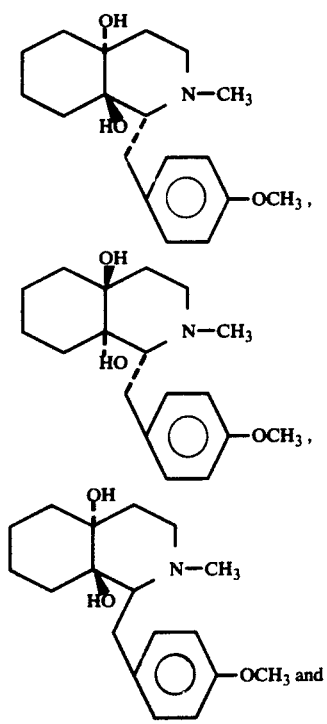

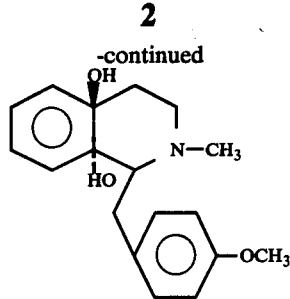

Nothing in this paper describes, anticipates or teaches the preparation of the 9,10-diols in which the N-methyl is alkanoyl as described herein. Furthermore, it is significant that the authors' goal was to synthesize 14-hydroxymorphinans via these diol intermediates and that they failed in their attempts, whereas the instant inventors have succeeded.

4. Schnider and Hellerback, Helv. Chim. Acta., 34, 2218–2222 (1951) describe the preparation of morphinans from the same starting materials as used in the instant invention. Nothing is taught or suggested that 14β-hydroxymorphinans could be prepared via this route.
5. Schnider, Brossi and Vogler, Helv. Chim. Acta., 37, 710–720 (1954) further describe the preparation of 14-deoxymorphinans from the same starting materials as used in the instant invention. Again, nothing is taught or suggested that 14β-hydroxymorphinans could be prepared via this route.
6. Schnider and Hellerback, Helv. Chim. Acta. 33, 1437–1448 (1950) describe the preparation of 14-deoxymorphinans from the same starting materials as used in the instant invention. Again, nothing is taught or suggested that 14β-hydroxymorphinans could be prepared via this route.
7. U.S. Pat. No. 3,919,237 reports the cyclization of compounds having the formulas

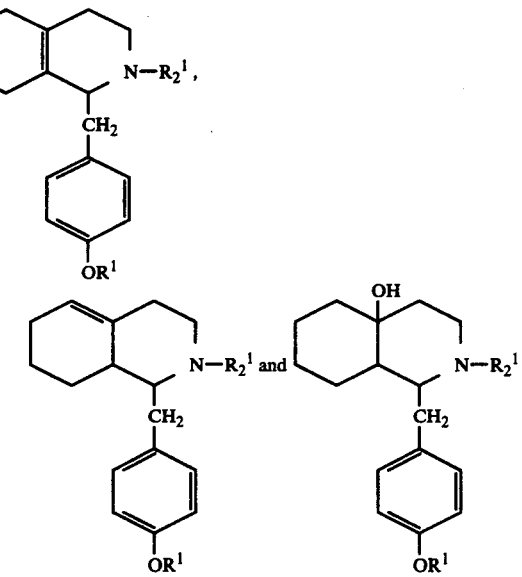

and derivatives thereof into isomorphinans and morphinans using boron trifluoride and a proton/hydronium ion donor as the cyclization catalyst. None of the compounds so produced have a 14β-hydroxy substituent.

SUMMARY OF THE INVENTION

This invention relates to a new process for the preparation of compounds having the formula

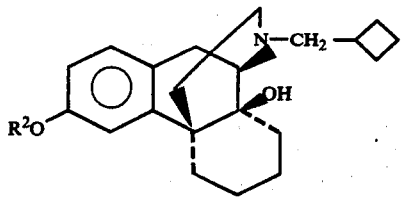

in which $R^2$ is H or (lower)alkyl; or an acid addition salt thereof from the starting material 2-(p-alkoxybenzyl)-1,2,3,4,5,6,7,8-octahydroisoquinoline.

COMPLETE DISCLOSURE

This invention relates to a new and novel synthesis of N-substituted-14-hydroxy-3-substituted-morphinans having the formula

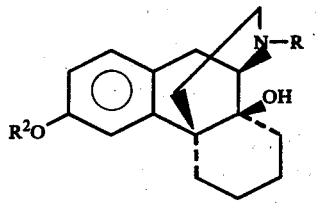

L in which $R^2$ is H or (lower)alkyl and R is cyclobutylmethyl or cyclopropylmethyl.

Drug abuse by thrill-seeking youth or by people looking for an escape from the realities of everyday life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was an object of the present invention to develop a method of synthesis for the above-described compounds characterized by Formula L that would not be dependent upon opium alkaloids as starting materials and yet would be commercially feasible.

The objectives of the present invention have been achieved by the process of preparing the compounds of Formula L by their total synthesis from readily available 2-(p-alkoxybenzyl)-1,2,3,4,5,6,7,8-octahydroisoquinoline starting material such as 2-(methoxybenzyl)-1,2,3,4,5,6,7,8-octahydroisoquinoline.

The compounds of the instant invention have the basic morphinan nucleus which is numbered and represented by the following plane formula:

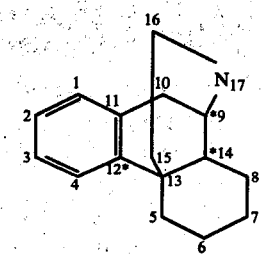

Although there are three asymetric carbons (asterisks) in the morphinan molecule, only two diastereoisomeric (racemic) forms are possible, because the iminoethano system, attached to position 9 and 13, is geometrically constrained to a cis-(1,3-diaxial)-fusion. These racemates can, therefore, differ only at the junction of rings B and C—in other words, in the configuration of carbon 14. The only variable will be the cis and trans relationship between the 5 (13) and 8 (14) bonds (Analgetics, Ed. George de Stevens, Academic Press, New York, p. 137 (1965)).

When, in the compounds of the present invention, the 5 (13) and 8 (14) bonds are cis to each other, we have compounds commonly designated as "morphinans". The use of a graphic representation of a "morphinan" is meant to include the dl racemic mixture and the resolved d and l isomers thereof.

The "morphinan" compounds of the present invention characterized by Formula L can each exist as two optical isomers, the levorotatory and dextrorotatory isomers. The optical isomers can be graphically illustrated as:

MORPHINANS

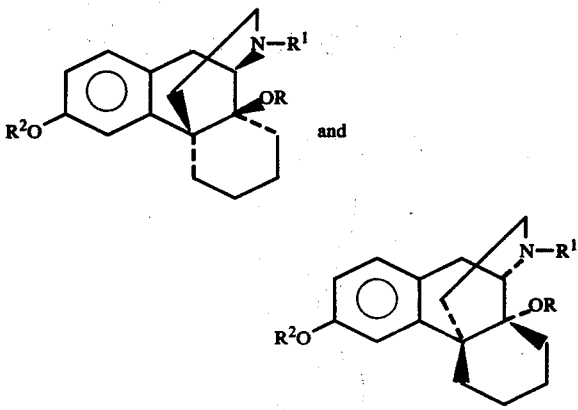

The present invention embodies all of the morphinan isomers including the optical isomers in their resolved form.

The optical isomers can be separated and isolated by fractional crystallization of the diastereoisomeric salts formed, for instance, with d- or l-tartaric acid or D-(+)-α-bromocamphor sulfonic acid. The levorotatory isomers of the compounds of the present invention are the most preferred embodiments.

For the purpose of this disclosure, the term "(lower)alkyl" is defined as an alkyl radical containing 1 to 6 carbon atoms, e.g., methyl, ethyl, propyl, isopropyl, n-butyl, iso-butyl, sec-butyl, etc. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of Formula L with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, naphthalenesulfonic, linoleic or linolenic acid, and the like.

The morphinan compounds LV (wherein R is cyclopropyl or cyclobutyl and $R^2$ is (lower)alkyl and LX (wherein R is cyclopropyl or cyclobutyl) of the instant invention are prepared by a total synthesis comprising 4–6 steps. The synthesis is efficient and appears commercially feasible. Chart I illustrates the process for the preparation of N-cyclobutylmethyl-3,14-dihydroxymorphinan (LXa) utilizing N-cyclobutylmethyl-14-hydroxy-3-methoxymorphinan (LVa).

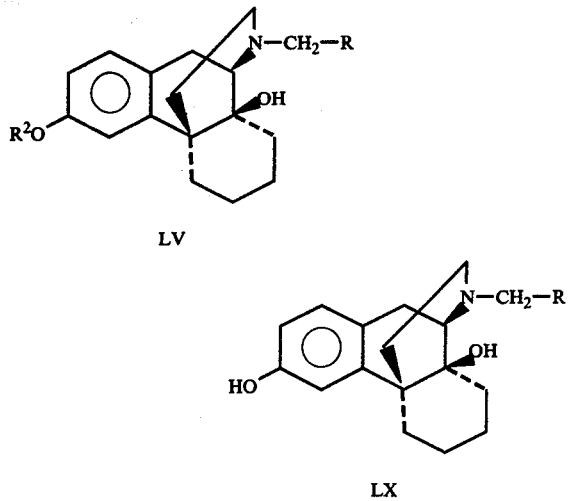

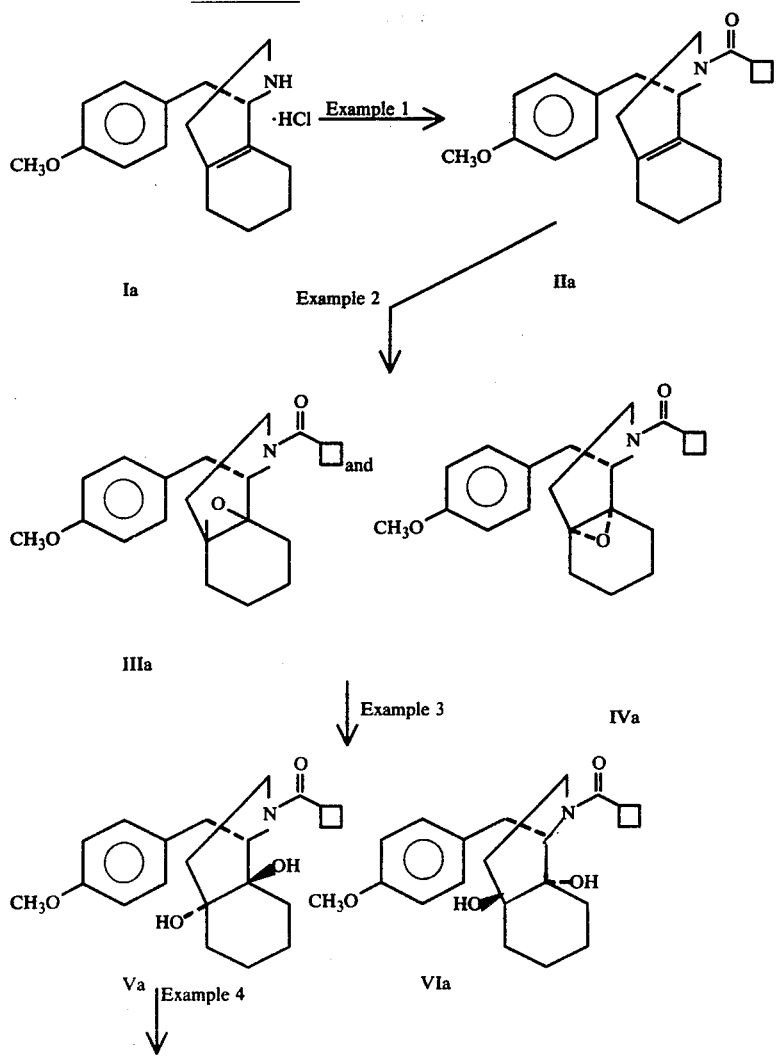

CHART I

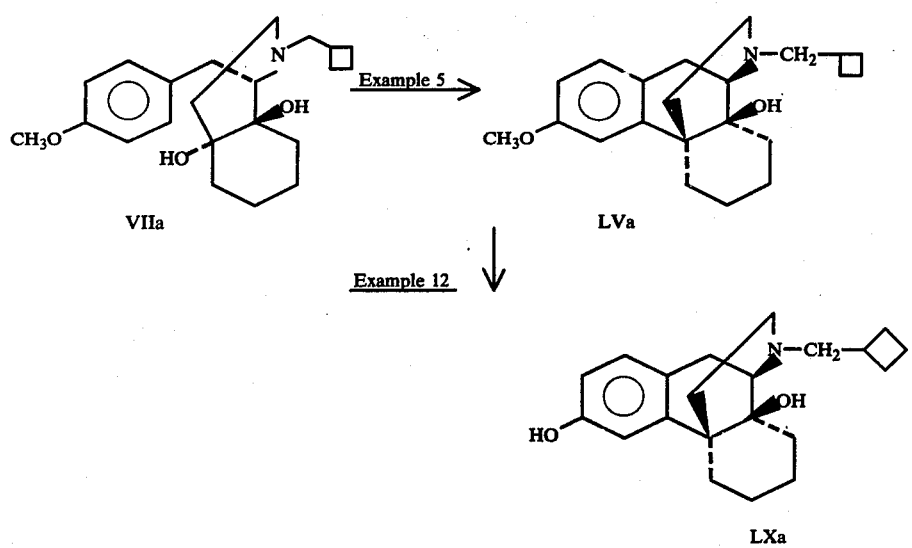

In opening the 9,10-epoxide group of compounds such as IIIa and IVa according to the procedure of Example 3, there are obtained 9,10-diol compounds capable of existing in conformations illustrated by the following planer formulas (and the four optical isomers thereof) wherein R is cyclobutyl or cyclopropyl and $R^2$ is (lower)alkyl.

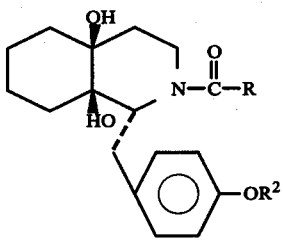

(cis-diol)

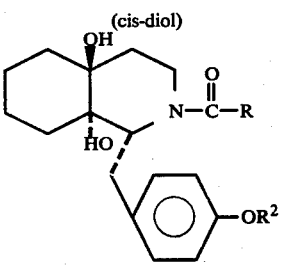

VI'
(trans-diol)

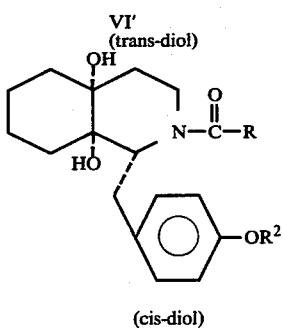

(cis-diol)

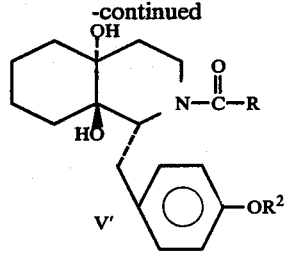

(trans-diol)

According to the process of the instant invention, it is thought that substantially all of the product obtained by the opening of the 9,10 epoxide group of compounds IIIa and IVa possesses the trans-9β,10α-diol relationship of compound Va (and its corresponding mirror image) with only a trace of the less desirable diol VIa.

A preferred embodiment of the present invention is the process for preparation of compounds having the formula

L wherein R is cyclobutyl or cyclopropyl and $R^2$ is H or (lower)alkyl comprising the consecutive steps of
(a) reducing the compound having the formula V

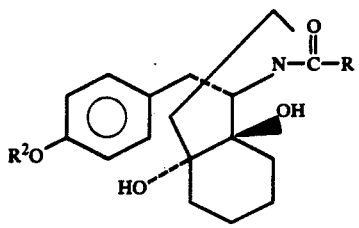

in which R is cyclobutyl or cyclopropyl and $R^2$ is (lower)alkyl with borane or a source of borane in an inert organic solvent to produce a boron complex of the compound having the formula VII

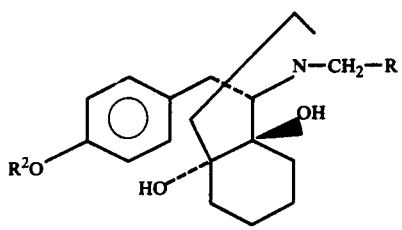

in which R is cyclobutyl or cyclopropyl and $R^2$ is (lower)alkyl;

(b) treating the boron complex of compound VII with acid to produce the compound having the formula LV

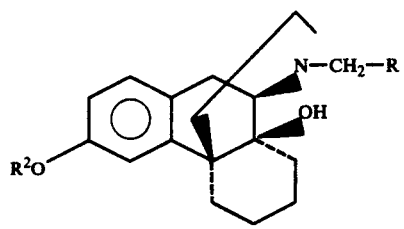

in which R is cyclobutyl or cyclopropyl and $R^2$ is (lower)alkyl; and, when desired, (c) cleaving the $R^2O$-ether function of compound LV by treating with $NaSC_2H_5$, hydrobromic acid, boron tribromide or pyridine hydrochloride to produce the compound having the formula LX

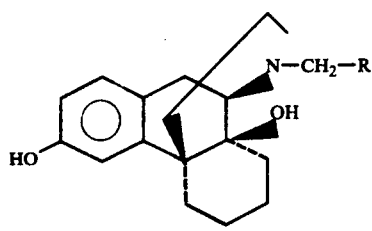

in which R is cyclopropyl or cyclobutyl.

Preferred embodiments of the foregoing process for preparation of compounds characterized by Formula L are those wherein:

(1) step (a) is carried out in tetrahydrofuran, toluene or benzene;

(2) in step (a), the formula V compound is reduced with borane dimethylsulfide;

(3) in step (a), the formula V compound is reduced with borane generating in situ by reacting sodium borohydride with a compound selected from the group of boron-trifluoride, boron-trifluoride tetrahydrofuran complex, or boron-trifluoride alkyletherate;

(4) in step (a) borane is employed in the ratio of about 1 mole of compound V to 1.33 to 2.0 moles of borane;

(5) in step (a) borane is employed in the ratio of about 1 mole of compound V to 1.6 to 1.9 moles of borane;

(6) in step (a) borane is employed in the ratio of about 1 mole of compound V to 1.75 moles of borane;

(7) step (a) is carried out with the aid of heat in the range of about 50°–115° C.

(8) step (a) is carried out in refluxing toluene;

(9) in step (b) the boron complex of compound VII is treated with an acid selected from the group consisting of phosphoric, orthophosphoric, pyrophosphoric, and polyphosphoric;

(10) in step (b) the boron complex of compound VII is treated with anhydrous phosphoric acid and phosphorous pentoxide;

(11) in step (b) the boron complex of compound VII is treated with a large excess of anhydrous phosphoric acid and phosphorous pentoxide;

(12) step (b) is carried out at a temperature in the range of 50°–100° C.;

(13) step (b) is carried out at a temperature in the range of 70°–75° C.;

(14) step (b) is carried out at a temperature in the range of 70°–75° C. with anhydrous phosphoric acid and phosphorous pentoxide.

Another preferred embodiment of the present invention is the process for the preparation of compounds having the formula

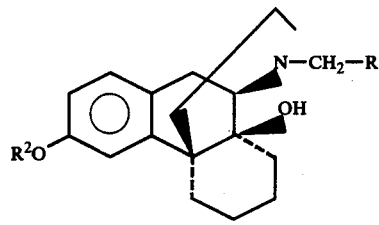

wherein R is cyclobutyl or cyclopropyl and $R^2$ is H or (lower)alkyl comprising the consecutive steps of (a) reducing the compound having the formula V

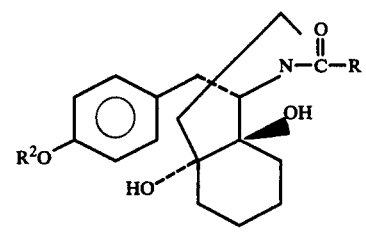

in which R is cyclobutyl or cyclopropyl and $R^2$ is (lower)alkyl with borane or a source of borane in an inert organic solvent to produce a boron complex of the compound having the formula VII

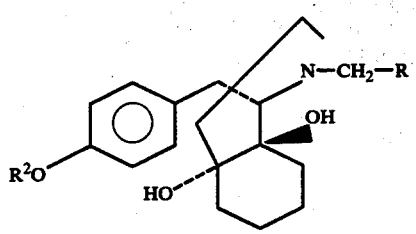

VII in which R is cyclobutyl or cyclopropyl and $R^2$ is (lower)alkyl;

(b) hydrolyzing the boron complex of compound VII with aqueous acid to provide compound VII;

(c) treating compound VII with an acid selected from the group consisting of phosphoric, orthophosphoric, pyrophosphoric, and polyphosphoric until cyclization is essentially complete to produce the compound having the formula LV

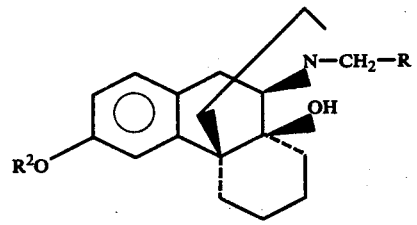

LV in which R is cyclobutyl or cyclopropyl and $R^2$ is (lower)alkyl; and, when desired, (d) cleaving the $R^2O$-ether function of compound LV by treating with $NaSC_2H_5$, hydrobromic acid, borontribromide or pyridine hydrochloride to produce the compound having the formula LX

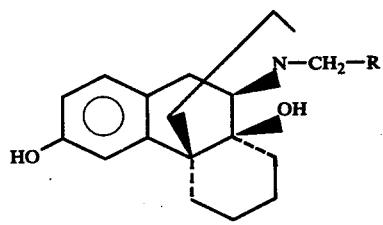

LX in which R is cyclobutyl or cyclopropyl.

Preferred embodiments of the above process for the preparation of compounds characterized by Formula L are those wherein:

(1) step (c) is carried out at a temperature in the range of 70°–90° C.; and (2) step (c) is carried out with anhydrous phosphoric acid at a temperature in the range of 80°–85° C.

The most preferred embodiment of the present invention is a process for the preparation of the compound having the formula L'

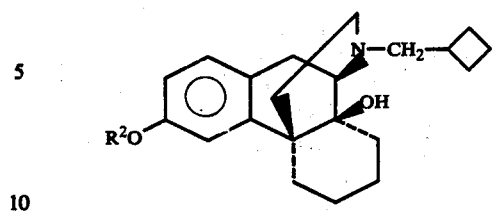

L' wherein $R^2$ is hydrogen or methyl comprising the consecutive steps of (a) reducing the compound having the formula Va

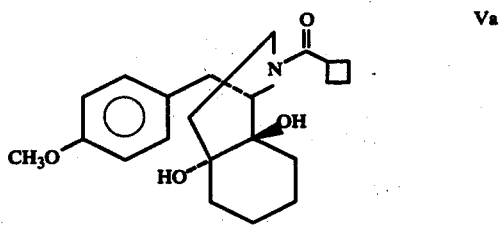

Va with borane in a molar ration of about 1.75 mole of borane to about 1 mole of compound Va in toluene with the aid of heat in the range of about 50°–115° C. to produce a boron complex of the compound having the formula VIIa

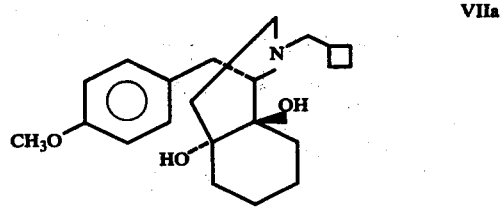

VIIa (b) treating the boron complex of compound VIIa with a large excess of a 6.4:1 mixture of anhydrous phosphoric acid:phosphorous pentoxide with the aid of heat in the range of about 70°–75° C. until cyclization is essentially complete to produce the compound having the formula LVa

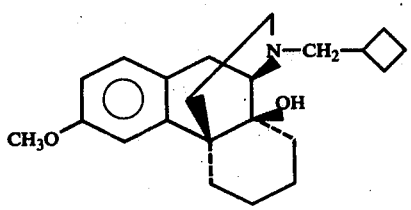

LVa and, when desired (d) demethylating compound LVa with $NaSC_2H_5$, hydrobromic acid, boron-tribromide or pyridine hydrochloride to produce the compound having the formula LXa

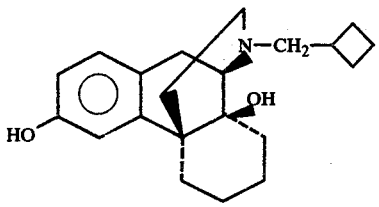

and, when desired (d) converting compound LXa into a nontoxic pharmaceutically acceptable acid addition salt thereof by methods known in the art.

The compounds N-cyclopropylmethyl-14β-hydroxy-3-methoxymorphinan, N-cyclobutylmethyl-14β-hydroxy-3-methoxymorphinan, N-cyclopropylmethyl-3,14β-dihydroxymorphinan and N-cyclobutylmethyl-3,14β-dihydroxymorphanin are known and described in the processes and examples of U.S. Pat. No. 3,819,635, which issued June 25, 1974.

For the purpose of this disclosure the term "inert organic solvent" means an organic solvent that does not participate in the reaction to the extent that it emerges unchanged from the reaction. Such solvents are methylene chloride, chloroform, dichlorethane, tetrachloromethane, benzene, toluene, ether, ethyl acetate, xylene, tetrahydrofuran dioxane, dimethylacetamide, and the like.

Experimental

All temperatures are expressed in degrees centigrade, VPC means vapor phase chromatography. IR means infrared spectrum. NMR means nuclear magnetic resonsance spectrum.

EXAMPLE 1

2-Cyclobutylcarbonyl-1-(p-methoxybenzyl)-1,2,3,4,5,6,7,8-octahydroisoquinoline (IIa)

Triethylamine (22.2 g., 0.22 mole) is slowly added to 1-(p-methoxybenzyl)-1,2,3,4,5,6,7,8-octahydroisoquinoline hydrochloride Ia (29.4 g., 0.1 mole) dissolved in 200 ml. of methylene chloride with stirring and ice-bath cooling. Cyclobutylcarbonyl chloride (13 g., 0.107 mole) in 30 ml. of methylene chloride is then added dropwise with stirring to the mixture while maintaining a temperature of 0° to 5° C. After stirring the reaction mixture for 1 hr. at room temperature, 100 ml. of water is added, the mixture acidified by adding 50 ml. of 10% sulfuric acid, and the methylene chloride layer separated. If desired, the methylene chloride solution containing IIa can be used for the next step directly or concentrated to give an oil which solidifies upon standing. Recrystallization of a sample of the solidified material from acetone provides crystalline product IIa, m.p. 89°-91°.

Various organic tertiary amines commonly employed as proton acceptors in acylation reactions may be substituted for triethylamine in the above procedure. Such amines are tri(lower)alkylamines, e.g., trimethylamine, triethylamine and the like, pyridine, dimethylaniline, N-methylpiperidine, and the like.

EXAMPLE 2

2-Cyclobutylcarbonyl-9,10-epoxy-1-(p-methoxybenzyl)perhydroisoquinolines (IIIa and IVa)

Method A — Peracetic acid oxidation

To a solution of 2-cyclobutylcarbonyl-1-(p-methoxybenzyl)-1,2,3,4,5,6,7,8-octahydroisoquinoline (IIa) (0.1 mole) in 230 ml. of methylene chloride is added peracetic acid (40%, 23.8 g., 0.12 mole) at such a rate so as to keep the temperature at 30°-35° C. After stirring the resulting solution at room temperature for 1 hr., 200 ml. of water is added and the excess peracetic acid destroyed by adding 100 ml. of 10% sodium bisulfite solution. The methylene chloride phase is separated and concentrated under reduced pressure to give an oily residue comprised of the isomeric epoxides trans IIIa and cis IVa in ratio of 23:78 according to vapor phase chromatography analysis (VPC). The two epoxides can be separated, if desired, by column chromatography using alumina or silica column (eluting with diethylether).

The minor epoxide (IIIa), m.p. 118°, has the "trans-configuration" and the major epoxide (IVa), m.p. 82°-84°, has the "cis configuration with respect to steric relationship of the p-methoxybenzyl group and the oxirane group.

Method B — Pertrifluoroacetic acid oxidation

To a solution of 2-cyclobutylcarbonyl-1-(p-methoxybenzyl)-1,2,3,4,5,6,7,8-octahydroisoquinoline (IIa) (0.05 mole) in 125 ml. of methylene chloride is added sodium carbonate (20 g., 0.19 mole) and the mixture cooled to 0°. A solution of pertrifluoroacetic acid is prepared by mixing trifluoroacetic anhydride (16.6 g., 0.077 mole) and 90% hydrogen peroxide (2.94 g., 0.077 mole) in 35 ml. of methylene chloride at 0°. The peracid solution is added to the reaction mixture of IIa dropwise at such a rate so as to maintain the reaction temperature at 0° to 5°. After completing the addition, the reaction mixture is stirred for a period of 0.5 hr. at 0° to 5° C. and excess peracid then destroyed by addition of 10% sodium bisulfite solution with agitation until the evaluation of $CO_2$ ceeased. The methylene chloride phase is washed with water, dried over anhydrous sodium sulfate and concentrated under reduced pressure to an oily residue comprised of the isomeric epoxides IIIa and IVa in a trans:cis ratio of 35:65 according to VPC.

EXAMPLE 3

2-Cyclobutylcarbonyl-9,10-dihydroxy-1-(p-methoxybenzyl)perhydroisoquinoline (Va and VIa)

The mixture of isomeric epoxides IIIa and IVa from peracetic acid oxidation of Example 2 is dissolved in 300 ml. of acetone and cooled to 0°. To this solution is first added 30 ml. of water and then 30 ml. of concentrated sulfuric acid at such a rate as to keep the temperature below 25°. After stirring the reaction mixture for a period of 1.5 hr. at 25°, a 150 ml. portion of water and a 300 ml. portion of toluene are added. The resulting two phase mixture is made basic with sodium hydroxide solution and the toluene layer separated and concentrated to a residue oil. This oil, stirred with 300 ml. of cyclohexane, provides a suspension of white solid which is collected on a filter. The white solid consists principally of the desired trans diol Va contaminated with the isomeric trans diol VIa as indicated by VPC.

The yield of Va calculated from the starting amine Ia is 75%. The cyclohexane filtrate is retreated with sulfuric acid to give another 10% yield of trans diol. Further purification of the white solid is carried out by crystallization from acetonitrile to provide material with m.p. 145°-147°. In place of the concentrated sulfuric acid used above, other acids such as nitric, hydrochloric, hydrobromic or strong organic acids such as alkylsulfonic, trifluoroacetic and the like may be employed.

Hydrolysis of the pure minor trans epoxide IIIa according to the above procedure gives only the desired trans diol Va while hydrolysis of the major cis epoxide IVa gives the desired trans diol Va with some of the isomeric trans diol VIa in a Va:VIa ratio of 86:14.

EXAMPLE 4

2-Cyclobutylmethyl-9,10-dihydroxy-1-(p-methoxybenzyl)perhydroisoquinoline (VIIa)

To a solution of 2-cyclobutylcarbonyl-9,10-dihydroxy-1-(p-methoxybenzyl)perhydroisoquinoline Va (30 g., 0.08 mole) in 300 ml. of tetrahydrofuran is added borane dimethylsulfide neat solution (14 ml., 0.14 mole) through a syringe needle under nitrogen atmosphere. The resulting mixture is heated to reflux for 2 hr. and then concentrated under reduced pressure to remove the solvent. The resulting borane complex of the cyclobutylmethyl amine VIIa can be used directly for the next reaction or it can be hydrolyzed with aqueous acid such as hydrochloric acid to provide VIIa, m.p. 120°-122° C. Reduction of the trans diol Va amido function with the following borane sources also provides VIIa.

(1) Borane-tetrahydrofuran complex.
(2) In 'situ' generated borane in tetrahydrofuran using sodium borohydride and boron trifluoride gas or boron trifluoride tetrahydrofuran complex or boron-trifluoride alkyletherate.

EXAMPLE 5

N-Cyclobutylmethyl-14β-hydroxy-3-methoxymorphinan (LVa)

Method A. Cyclization with borane complex

To the borane complex residue from borane reduction reaction (0.08 mole) of Example 4 is added 320 g. of anhydrous phosphoric acid (prepared from 85% phosphoric acid and phosphorous pentoxide) and 50 g. of phosphorous pentoxide. The mixture is stirred at room temperature for 0.5 hr. and then at 70°-75° for a period of 4 hr. The reaction mixture is diluted with 200 ml. of water and then poured into a mixture of 600 ml. of concentrated ammonium hydroxide and 1 liter of crushed ice. The mixture is extracted with 400 ml. of heptane and the heptane extract dried over sodium sulfate. Concentration of the dried heptane extract provides 23.1 g. of oil (85% yield) of product LVa. This oil is dissolved in acetone and treated with anhydrous hydrogen chloride gas to afford crystalline hydrochloride salt of product LVa, m.p. 248°-250°.

Method B. Cyclization without boron complex of any kind 1.5 g. of 2-Cyclobutylmethyl-9,10-dihydroxy-1-(p-methoxybenzyl)perhydroisoquinoline VIIa and 16.0 g. of anhydrous phosphoric acid are stirred at 80°-85° for 23 hr. The reaction mixture is diluted with 20 ml. of water and poured into a mixture of ice and 35 ml. of concentrated ammonium hydroxide. The mixture is extracted with 40 ml. of methylene chloride and the methylene chloride extract concentrated to give 1.15 g. of oil. According to vapor phase chromatography-mass spectrometry analysis, the oil contained 57% of the desired N-cyclobutylmethyl-14β-hydroxy-3-methoxymorphinan LVa, 27% of a dehydrated by-product and 15% of uncyclized VIIa starting material.

EXAMPLE 6

Levorotatory-N-Cyclobutylmethyl-14β-hydroxy-3-methoxymorphinan (LVa').

Substitution in the procedure of Example 1 of dextrorotatory-1-(p-methoxybenzyl)-1,2,3,4,5,6,7,8-octahydroisoquinoline hydrochloride for racemic Ia and sequentially applying the procedures of Examples 2–5 provides the levorotatory product LVa'.

The procedures of Examples 4 and 5 are carried out as follows. To a solution of levorotatory-2-cyclobutylcarbonyl-9,10-dihydroxy-2-(p-methoxybenzyl)perhydroisoquinoline (10 g., 0.0267 mole) in 100 ml. of toluene is added borane dimethylsulfide neat solution (6 ml., 0.057 mole) through a syringe needle under nitrogen atmosphere. The resulting solution is refluxed for 3 hr., concentrated under reduced pressure to remove approximately 40 ml. of solvent and the borane complex of levorotatory cyclobutylmethyl amine VIIa' is used directly in the cyclization reaction.

Cyclization of the levorotatory-cyclobutylmethyl amine VIIa' is carried out by adding the above toluene-borane complex mixture portionwise to 200 g. of anhydrous phosphoric acid and 35 g. of phosphorus pentoxide with stirring while maintaining a temperature range of 0°-25° C. After the addition is complete, the mixture is heated and stirred for a period of 5 hr. at 70° C. and then poured into a mixture of 400 ml. of concentrated ammonium hydroxide with sufficient ice to maintain a temperature of approximately 25° C. The mixture is extracted with toluene, the toluene extract washed with water and then concentrated under reduced pressure to provide levorotatory-N-cyclobutylmethyl-14β-hydroxy-3-methoxy-morphinan (LVa') base. The oily base is converted to the sulfate salt by treating with sulfuric acid to accord 7.2 g. (61% yield) of levorotatory-N-cyclobutylmethyl-14β-hydroxy-3-methoxy-morphinan, m.p. 232°-237° C. (dec.), $[\alpha]_d$ −55.4° C. (C = 0.56, $CH_3OH$).

EXAMPLE 7

2-Cyclopropylcarbonyl-1-(p-methoxybenzyl)-1,2,3,4,5,6,7,8-octahydroisoquinoline (IIb)

Substitution in the procedure of Example 1 for the cyclobutylcarbonyl chloride used therein of an equimolar quantity of cyclopropylcarbonyl chloride produces the title material IIb.

EXAMPLE 8

2-Cyclopropylcarbonyl-9,10-epoxy-1-(p-methoxybenzyl)perhydroisoquinolines (IIIb and IVb)

Substitution in the procedure of Example 2 for the racemic IIa used therein of an equimolar quantity of IIb produces the title compounds IIIb and IVb.

EXAMPLE 9

2-Cyclopropylcarbonyl-9,10-dihydroxy-1-(p-methoxybenzyl)perhydroisoquinoline (Vb, VIb)

Substitution in the procedure of Example 3 for the racemic IIIa and IVb used therein of an equimolar quantity of IIIb and IVb produces the title compounds Vb and VIb.

EXAMPLE 10

2-Cyclopropylmethyl-9,10-dihydroxy-1-(p-methoxybenzyl)perhydroisoquinoline (VIIb)

Substitution in the procedure of Example 4 for the racemic Va used therein of an equimolar quantity of Vb produces the title compound VIIb.

EXAMPLE 11

N-Cyclopropylmethyl-14β-hydroxy-3-methoxymorphinan (LVb)

Substitution in the procedure of Example 5 for the racemic VIIa used therein of an equimolar quantity of VIIb produces the title product LVb.

EXAMPLE 12

N-Cyclobutylmethyl-3,14-dihydroxymorphinan (LXa)

A mixture of N-cyclobutylmethyl-14β-hydroxy-3-methoxymorphinan (LVa) (1.0 g., 2.58 m mole) and 10 ml. of 48% HBr is refluxed under a nitrogen atmosphere for a period of five minutes. After cooling, the reaction mixture is diluted with water and made basic with aqueous ammonium hydroxide. The aqueous basic mixture is extracted with several portions of chloroform and the combined chloroform extracts dried over anhydrous sodium sulfate. After evaporating the solvent, the residual oil (730 mg.) is taken up in dry ether and the resulting solution filtered through diatomaceous earth-charcoal. The filtrate is treated with a saturated solution of hydrogen chloride in dry ether and the hydrochloride salt thus obtained is collected and crystallized from methanol-acetone to afford 565 mg. (56.5%) of N-cyclobutylmethyl-3,14-dihydroxymorphinan hydrochloride (LXa), m.p. 272°–274° (dec.). The IR and NMR spectra were consistent with the structure.

Analysis.—Calcd. for $C_{21}H_{29}NO_2 \cdot HCl \cdot \frac{1}{4}CH_3OH$ (percent): C, 67.97; H, 8,49; N, 3.49. Found (percent): C, 68.10; H, 8.14; N, 3.80.

Acidification of the filtered dry ether solution referred to above with appropriate acids provides various "pharmaceutically acceptable acid addition salts" of LXa.

The 3-methoxy ether function of N-cyclobutylmethyl-14β-hydroxy-3-methoxymorphinan may also be cleaved by treatment with ether cleaving agents such as $NaSC_2H_5$, boron tribromide, or pyridine hydrochloride to produce the desired demethylated product LXa.

What is claimed is:

1. A process for the preparation of compounds having the formula

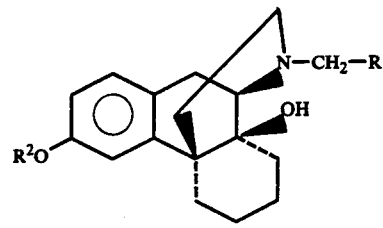

wherein R is cyclobutyl or cyclopropyl and $R^2$ is H or (lower)alkyl comprising the consecutive steps of (a) reducing the compound having the formula V

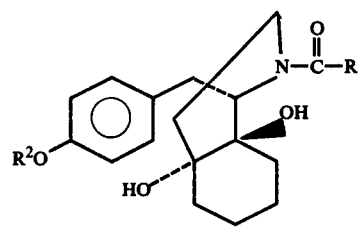

in which R is cyclobutyl or cyclopropyl and $R^2$ is (lower)alkyl with borane in an inert organic solvent to produce a boron complex of the compound having the formula VII

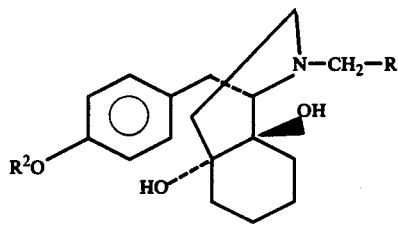

in which R is cyclobutyl or cyclopropyl and $R^2$ is (lower)alkyl;

(b) treating the boron complex of compound VII with acid to produce the compound having the formula LV

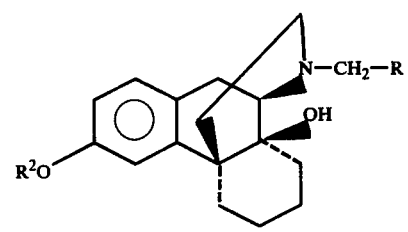

in which R is cyclobutyl or cyclopropyl and $R^2$ is (lower)alkyl; and, when desired, (c) cleaving the $R^2O$-ether function of compound LV by treating with $NaSC_2H_5$, hydrobromic acid, boron tribromide or pyridine hydrochloride to produce the compound having the formula LX

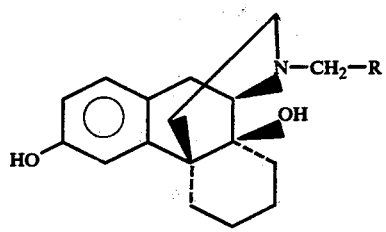

LX in which R is cyclobutyl or cyclopropyl.

2. The process of claim 1 wherein step (a) is carried out in toluene.

3. The process of claim 1 wherein in step (a) the formula V compound is reduced with borane dimethylsulfide.

4. The process of claim 1 wherein in step (a) the formula V compound is reduced with boron generated in situ by reacting sodium borohydride and boron trifluoride or sodium borohydride and boron-trifluoride tetrahydrofuran complex or sodium borohydride and boron-trifluoride alkyletherate.

5. The process of claim 1 wherein in step (a) borane is employed in a ratio of about 1 mole compound V to 1.33 to 2.0 moles of borane.

6. The process of claim 1 wherein in step (a) borane is employed in a ratio of about 1 mole of compound V to 1.6 to 1.9 moles of borane.

7. The process of claim 1 wherein in step (a) borane is employed in a ratio of about 1 mole of compound V to 1.75 moles of borane.

8. The process of claim 1 wherein step (a) is carried out with the aid of heat in the range of about 50° to 115° C.

9. The process of claim 1 wherein step (a) is carried out in refluxing toluene.

10. The process of claim 1 wherein in step (b) the boron complex of compound VII is treated with an acid selected from the group consisting of phosphoric, orthophosphoric, pyrophosphoric, and polyphosphoric.

11. The process of claim 1 wherein in step (b) the boron complex of compound VII is treated with anhydrous phosphoric acid and phosphorous pentoxide.

12. The process of claim 1 wherein in step (b) the boron complex of compound VII is treated with a large excess of anhydrous phosphoric acid and phosphorous pentoxide.

13. The process of claim 1 wherein step (b) is carried out at a temperature in the range of 50° to 100° C.

14. The process of claim 1 wherein step (b) is carried out at a temperature in the range of 70°-75° C.

15. The process of claim 1 wherein step (b) is carried out at a temperature in the range of 70°-75° C. with anhydrous phosphoric acid and phosphorous pentoxide.

16. A process for the preparation of compounds having the formula

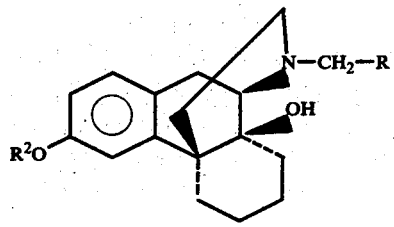

L wherein R is cyclobutyl or cyclopropyl and $R^2$ is H or (lower)alkyl comprising the consecutive steps of (a) reducing the compound having the formula V

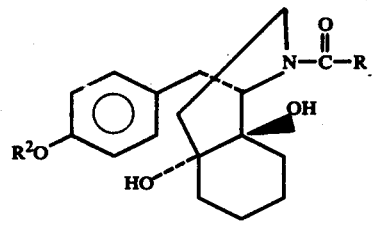

V in which R is cyclobutyl or cyclopropyl and $R^2$ is (lower)alkyl with borane in an inert organic solvent to produce a boron complex of the compound having the formula VII

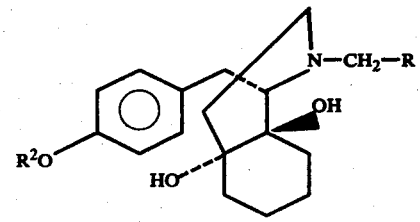

VII in which R is cyclobutyl or cyclopropyl and $R_2$ is (lower)alkyl;

(b) hydrolyzing the boron complex of compound VII with aqueous acid to provide compound VII;

(c) treating compound VII with an acid selected from the group consisting of phosphoric, orthophosphoric, pyrophosphoric, and polyphosphoric to produce the compound having the formula LV

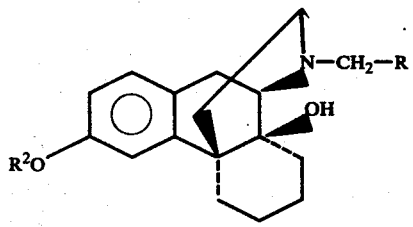

LV in which R is cyclobutyl or cyclopropyl and $R^2$ is (lower)alkyl; an, when desired, (d) cleaving the $R^2O$-ether function of compound LV by treating with $NaSC_2H_5$, hydrobromic acid, boron-tribromide or pyridine hydrochloride to produce the compound having the formula LX

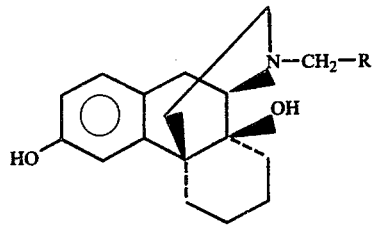

in which R is cyclobutyl or cyclopropyl.

17. The process of claim 16 wherein step (c) is carried out at a temperature in the range of 70°–90° C.

18. The process of claim 16 wherein step (c) is carried out with anhydrous phosphoric acid at a temperature in the range of 80°–85° C.

19. A process for the preparation of the compound having the formula (L')

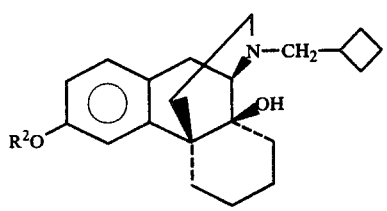

wherein $R^2$ is hydrogen or methyl comprising the consecutive steps of (a) reducing the compound having the formula Va

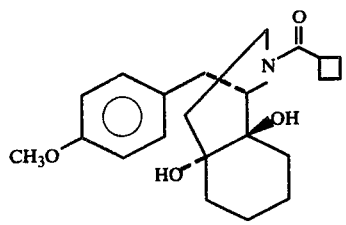

with borane in a molar ratio of about 1.75 mole of borane to about 1 mole of compound Va in toluene with the aid of heat in the range of about 50°–115° C. to produce a boron complex of the compound having the formula VIIa

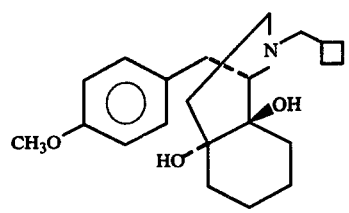

(b) treating the boron complex of compound VIIa with a large excess of a 6.4:1 mixture of anhydrous phosphoric acid:phosphorous pentoxide with the aid of heat in the range of about 70°–75° C. until the cyclization is essentially complete to produce the compound having the formula LVa

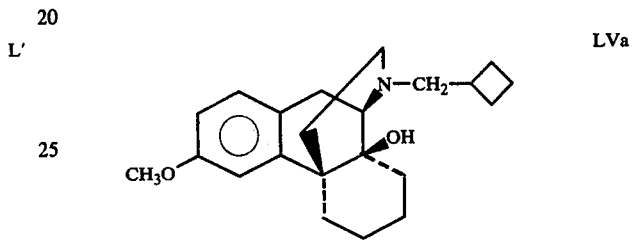

and, when desired, (c) demethylating compound LVa with $NaSC_2H_5$, hydrobromic acid, boron-tribromide or pyridine hydrochloride to produce the compound having the fromula LXa

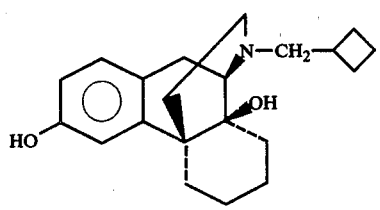

* * * * *